United States Patent
Hudson et al.

(10) Patent No.: US 10,558,760 B2
(45) Date of Patent: *Feb. 11, 2020

(54) UNSUPERVISED TEMPLATE EXTRACTION

(71) Applicant: International Business Machines Corporation, Armonk, NY (US)

(72) Inventors: Eddy Hudson, Austin, TX (US); Joseph M. Kaufmann, Austin, TX (US); Niyati Parameswaran, Santa Clara, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/791,009

(22) Filed: Oct. 23, 2017

(65) Prior Publication Data

US 2019/0034410 A1    Jan. 31, 2019

Related U.S. Application Data

(63) Continuation of application No. 15/662,701, filed on Jul. 28, 2017.

(51) Int. Cl.
*G06F 17/27* (2006.01)
*G06F 17/21* (2006.01)
(Continued)

(52) U.S. Cl.
CPC ......... *G06F 17/279* (2013.01); *G06K 9/6218* (2013.01); *G06K 9/726* (2013.01); *H04L 51/02* (2013.01)

(58) Field of Classification Search
CPC ......... G06F 17/30675; G06F 17/30713; G06F 17/30616; G06F 17/28881; G06F 17/30; G06F 17/30554; G06F 17/30705
(Continued)

(56) References Cited

U.S. PATENT DOCUMENTS 5,920,856 A * 7/1999 Syeda-Mahmood ... G06F 16/40
6,601,026 B2    7/2003 Appelt et al.
(Continued)

FOREIGN PATENT DOCUMENTS

| CN | 103514292 | 1/2014 |
| CN | 104636431 | 5/2015 |
| CN | 105183721 | 12/2015 |

OTHER PUBLICATIONS

Lin "Automatic retrieval and clustering of similar words.", 1998, In Proceedings of the 17th international conference on Computational linguistics—vol. 2. Association for Computational Linguistics, 1998, pp. 768-774.*

(Continued)

*Primary Examiner* — Olujimi A Adesanya
(74) *Attorney, Agent, or Firm* — VanLeeuwen & VanLeeuwen; Diana R. Gerhardt

(57) ABSTRACT

An approach is provided that improves a question answering (QA) computer system by automatically generating relationship templates. Event patterns are extracted from data in a corpus utilized by the QA computer system. The extracted event patterns are analyzed with the analysis resulting in a number of clusters of related event patterns. Relationship templates are then created from the plurality of clusters of related event patterns and these relationship templates are then utilized to visually interact with the corpus.

7 Claims, 9 Drawing Sheets

(51) Int. Cl.
*G06K 9/62* (2006.01)
*G06K 9/72* (2006.01)
*H04L 12/58* (2006.01)

(58) Field of Classification Search
USPC .......................................................... 704/9
See application file for complete search history.

(56) References Cited

U.S. PATENT DOCUMENTS

| | | | |
|---|---|---|---|
| 7,379,946 B2 | 5/2008 | Carus et al. | |
| 8,108,439 B2* | 1/2012 | Guo | G06F 16/954 707/802 |
| 8,230,323 B2 | 7/2012 | Bennett et al. | |
| 8,285,619 B2 | 10/2012 | Herz et al. | |
| 8,825,471 B2 | 9/2014 | Betz et al. | |
| 9,037,607 B2 | 5/2015 | Chew | |
| 9,043,197 B1* | 5/2015 | Pasca | G06F 17/30654 704/10 |
| 9,268,844 B1* | 2/2016 | Kadarkarai | G06F 17/30705 |
| 10,394,936 B2* | 8/2019 | Bergman | G06F 16/367 |
| 2003/0018652 A1* | 1/2003 | Heckerman | G06F 17/30713 |
| 2006/0009966 A1 | 1/2006 | Johnson et al. | |
| 2008/0114800 A1 | 5/2008 | Gazen | G06F 17/3071 |
| 2010/0005124 A1* | 1/2010 | Wagner | G06F 16/27 707/E17.005 |
| 2010/0313157 A1* | 12/2010 | Carlsson | G06F 16/287 715/769 |
| 2011/0238410 A1* | 9/2011 | Larcheveque | G06F 17/2785 704/9 |
| 2012/0054226 A1* | 3/2012 | Cao | G06F 16/34 707/769 |
| 2014/0195884 A1 | 7/2014 | Castelli et al. | |
| 2015/0142704 A1* | 5/2015 | London | G06F 16/90332 706/11 |
| 2015/0161230 A1* | 6/2015 | Alkov | G06F 17/30705 707/737 |
| 2015/0269138 A1* | 9/2015 | Parris | G06F 16/367 704/9 |
| 2015/0347557 A1* | 12/2015 | Allen | G06F 17/30598 707/738 |
| 2016/0012818 A1* | 1/2016 | Faizakof | G10L 15/063 704/245 |
| 2016/0019885 A1* | 1/2016 | Romano | G06F 17/214 704/9 |
| 2016/0140439 A1* | 5/2016 | Adderly | G06N 5/02 706/46 |
| 2016/0342677 A1* | 11/2016 | Nuchia | G06F 17/30598 |
| 2017/0161619 A1* | 6/2017 | Franceschini | G06N 5/022 |
| 2017/0286832 A1* | 10/2017 | Ho | G06F 17/30401 |

OTHER PUBLICATIONS

Lu et al., Automatic Event Extraction with Structured Preference Modeling, Proceedings of the 50th Annual Meeting of the Association for Computational Linguistics, Jeju, Republic of Korea, Jul. 2012, pp. 835-844.

Walter et al., "Fast Agglomerative Clustering for Rendering," IEEE Symposium on Interactive Ray Tracing 2008, Los Angeles, CA, Aug. 2008, 6 pages.

"List of IBM Patents or Patent Applications Treated as Related," Letter from Leslie A. Van Leeuwen, Oct. 23, 2017, 1 page.

Hudson et al., "Unsupervised Template Extraction," U.S. Appl. No. 15/662,701, filed Jul. 28, 2017, 41 pages.

* cited by examiner

UNSUPERVISED TEMPLATE EXTRACTION

BACKGROUND

The increasing amount of information that is stored in electronic form has caused Information Extraction to emerge as a crucial tool when attempting to detect, extract and truly understand specific categories of information in a natural language document. Information Extraction is used in question-answering (QA) systems to load information in the QA system's corpus. Templates have been used in Natural Language Processing (NLP) for quite some time. They are currently being used in QA systems to generate more question answer pairs. Templates can also be used in topic modeling where the level of granularity in the templates created can be modified to suit the domain that is being examined.

One approach used to address Information Extraction is the creation of a series of shallow text analysis rules which are typically based on pre-defined linguistic patterns. This involves the creation of syntactic rules between words and exploits the semantic classes of words to capture concepts and events which may be of interest to the user. However, the acquisition of such domain specific knowledge and the development of such specific rules constitute an extremely time consuming task. Moreover, these tasks are restricted to specific applications and require vast amounts of manual intervention.

BRIEF SUMMARY

An approach is provided that improves a question answering (QA) computer system by automatically generating relationship templates. Event patterns are extracted from data in a corpus utilized by the QA computer system. The extracted event patterns are analyzed with the analysis resulting in a number of clusters of related event patterns. Relationship templates are then created from the plurality of clusters of related event patterns and these relationship templates are then utilized to visually interact with the corpus.

The foregoing is a summary and thus contains, by necessity, simplifications, generalizations, and omissions of detail; consequently, those skilled in the art will appreciate that the summary is illustrative only and is not intended to be in any way limiting. Other aspects, inventive features, and advantages of the present disclosure, as defined solely by the claims, will become apparent in the non-limiting detailed description set forth below.

In traditional approaches, most of the work with templates in the Information Extraction space works on generating such templates manually. Parts of the work have been automated with the use of seed examples, but even then, with the amount of human involvement required, the scalability of the entire process takes a hit. There have also been attempts to fully automate the template extraction process, with distance based clustering and probabilistic modeling. But with distance based clustering the additional step of corpus expansion becomes a must, and with probabilistic modeling, the results suffer from low precision.

BRIEF DESCRIPTION OF THE SEVERAL VIEWS OF THE DRAWINGS

The present disclosure may be better understood, and its numerous objects, features, and advantages made apparent to those skilled in the art by referencing the accompanying drawings, wherein.

DETAILED DESCRIPTION

Figure 1:
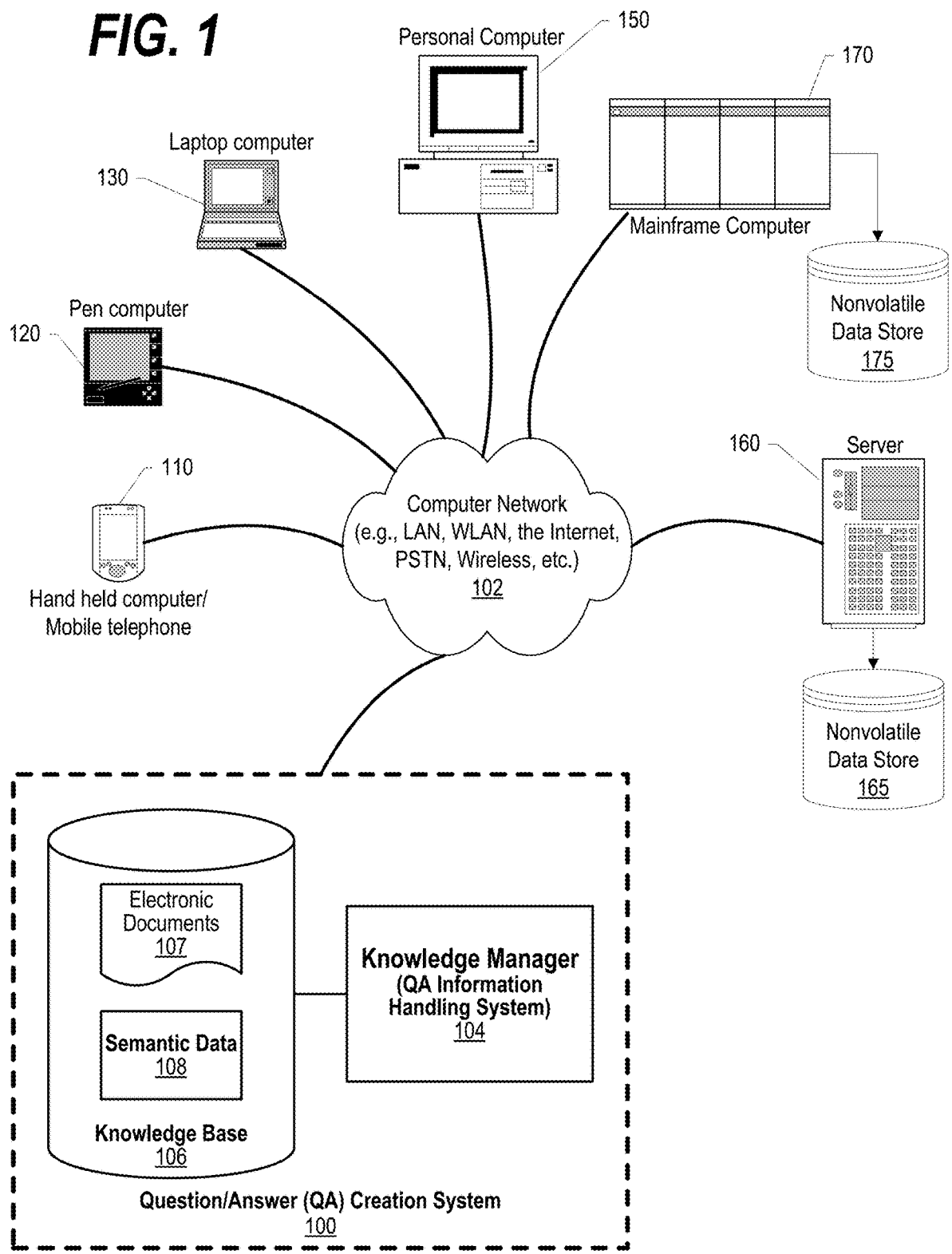
FIG. 1 depicts a schematic diagram of one illustrative embodiment of a question answering (QA) system in a computer network.

FIGS. 1-9 depict an approach that provides a system and method for unsupervised template extraction. The approach automatically generates rules for Information Extraction in the form of templates. Templates are essentially a way of representing scenarios and are defined by the events that take place in the scenario, and the roles used in those events. For example, in a "bombing" template, the events involved would be 'bomb', 'destroy', 'injure', etc. And some of the roles involved would be the place that gets bombed, the person responsible for the bomb, etc. Each of the roles in a template has different relationships with the other roles in the template at a syntactic, semantic, and pragmatic level.

Natural language processing (NLP) is applied to a set of text to determine event patterns. The patterns are analyzed by a hierarchical similarity and distance algorithm to create groups or clusters of related event patterns. These related event patterns are further refined using argument similarity in order to create relationship templates. The refined relationships are based on converting arguments into vectors and using distributional semantics against those vectors. The templates are used to generate ground truth candidates by comparing them against other sources.

This approach provides a novel way of constructing templates automatically without manual intervention. Not only does the proposed system create term-based extraction patterns and exploit syntax on a natural language parse, it also captures semantics by learning the semantic mappings prevalent in dictionaries. Moreover, this approach combines distance based clustering with distributional semantics in a novel manner thereby tremendously reducing the dependence of the template extraction system that has been proposed on corpus expansion.

Apart from successfully eliminating the need for corpus expansion the proposed methodology also boosts performance accuracy when extracting templates as the approach learns a more accurate representation of the concepts present in the source by tapping into context, words, and collocations thereby providing better case frames for terms. In addition, this approach exploits semantic hierarchical information for eventual generalization or even sub-categorization of the template patterns.

Thus the proposed template extraction system is unique in its ability to generate templates with higher efficiency, lower computational cost and minimal human intervention. The approach provides a system for extracting templates from unstructured natural language text. With automatic generation of templates, question generation systems have access to a larger set of templates, with less effort. The automatic generation of templates can also represent a way of summarizing large pieces of text. When viewed through a user interface (UI), the generated templates allow the user to explore the various scenarios in the input text in a more visually appealing manner, as opposed to viewing bland lines of text. Using the UA, the user can also explore the relationships present in the input text. Furthermore, this approach also helps users accumulate more training data for training relationship extraction services.

The approach described herein can be utilized by companies and organizations with large textual corpora to efficiently and effectively wade through the organization's corpora. Summarization of large text into shorter and grammatically correct pieces of text is beneficial. While traditional summarizations are easier to read, they often do not convey an accurate idea of the content in the corpus. Traditional summarizations allow for a small window through which the reader can view what the underlying text might contain. Using the templates generated from the approach described herein, on the other hand, contain important relationships, roles, and events within the corpora. The information provided by this approach achieves these benefits while simultaneously maintaining a reduction in the total amount of text. Thus, templates generated using this approach represent a better alternative to summarization. Consequently, these templates can be used for corpus exploration by companies and other organizations with large corpora.

Corpus exploration is permitted in this embodiment through a user interface (UI). The UI consists of three screens: the main screen, the zoomed view, and the focused view. The main screen contains all the templates extracted from the input text. Each template gets a circle in the main screen. The intensity of the color is directly proportional to the quality of the template. The stronger the color, the better the template. Each circle in the main screen contains the key events which happen in the template represented by the circle. The zoomed view shows the more detailed view of a template. It can be reached by clicking the circle representing a template. It includes one large circle in the middle which contains all the events in the template. The large circle in the middle is surrounded by multiple smaller circular islands, each of which represents a role within the template. Each circular island contains an example of that role within the input corpus. Finally, the focused view is a more detailed view of a role within a template. It can be reached by clicking one of the circular islands in the zoomed view. In this view, the clicked circular island will contain more examples of the role that can be found in the input text. Instead of all the events in the template, the large central circle will contain only those events of which the clicked role is a part of. The tense of the verbs will also change to show the relation of the role to the verb. If the role is a subject, the verb will be in present tense. If the role is an object, then the verb will be in the passive voice. Finally, if the role is a prepositional object, the verb will be in passive voice, and the preposition involved will be appended to the verb.

The embodiment used for corpus exploration can also be used to help generate training data for relationship extraction services. Traditionally, training data for relationship extraction services required human beings to traverse through large portions of text, pick out examples of relationships and add them to the training dataset. Using the approach provided herein, however, humans operators are able to receive a rough idea of the relationships in the input corpus. Thus, the operators know what they are looking for as they are scanning the large sections of text. The approach could also let the human annotators know where to find examples of particular relationships within the corpus. Therefore, this approach reduces the amount of time needed to accumulate training data for relationship extractions services.

The approach described herein can also assist question generators generate more question-answer pairs. Traditional question generators have paraphrasing mechanisms using templates. However, the templates used are manually generated. This severely limits the reach of question generators across domains and depth of text. With this approach, templates are automatically generated that can then be used by question generators to generate more questions across domains and more pieces of text.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions. The following detailed description will generally follow the summary of the disclosure, as set forth above, further explaining and expanding the definitions of the various aspects and embodiments of the disclosure as necessary.

FIG. 1 depicts a schematic diagram of one illustrative embodiment of a question/answer (QA) system 100 in a computer network 102. QA system 100 may include knowledge manager 104, which comprises one or more processors and one or more memories, and potentially any other computing device elements generally known in the art including buses, storage devices, communication interfaces, and the like. Computer network 102 may include other computing devices in communication with each other and with other devices or components via one or more wired and/or wireless data communication links, where each communication link may comprise one or more of wires, routers, switches, transmitters, receivers, or the like. QA system 100 and network 102 may enable question/answer (QA) generation functionality for one or more content users. Other embodiments may include QA system 100 interacting with components, systems, sub-systems, and/or devices other than those depicted herein.

QA system 100 may receive inputs from various sources. For example, QA system 100 may receive input from the network 102, a corpus of electronic documents 107 or other data, semantic data 108, and other possible sources of input.

In one embodiment, some or all of the inputs to QA system 100 route through the network 102 and stored in knowledge base 106. The various computing devices on the network 102 may include access points for content creators and content users. Some of the computing devices may include devices for a database storing the corpus of data. The network 102 may include local network connections and remote connections in various embodiments, such that QA system 100 may operate in environments of any size, including local and global, e.g., the Internet. Additionally, QA system 100 serves as a front-end system that can make available a variety of knowledge extracted from or represented in documents, network-accessible sources and/or structured data sources. In this manner, some processes populate the knowledge manager with the knowledge manager also including input interfaces to receive knowledge requests and respond accordingly.

In one embodiment, a content creator creates content in a document 107 for use as part of a corpus of data with QA system 100. The document 107 may include any file, text, article, or source of data for use in QA system 100. Content users may access QA system 100 via a network connection or an Internet connection to the network 102, and may input questions to QA system 100, which QA system 100 answers according to the content in the corpus of data. As further described below, when a process evaluates a given section of a document for semantic content, the process can use a variety of conventions to query it from knowledge manager 104. One convention is to send a well-formed question.

Semantic data 108 is content based on the relation between signifiers, such as words, phrases, signs, and symbols, and what they stand for, their denotation, or connotation. In other words, semantic data 108 is content that interprets an expression, such as by using Natural Language Processing (NLP). In one embodiment, the process sends well-formed questions (e.g., natural language questions, etc.) to QA system 100 and QA system 100 may interpret the question and provide a response that includes one or more answers to the question. In some embodiments, QA system 100 may provide a response to users in a ranked list of answers.

In some illustrative embodiments, QA system 100 may be the IBM Watson™ QA system available from International Business Machines Corporation of Armonk, N.Y., which is augmented with the mechanisms of the illustrative embodiments described hereafter. The IBM Watson™ knowledge manager system may receive an input question which it then parses to extract the major features of the question, that in turn are then used to formulate queries that are applied to the corpus of data. Based on the application of the queries to the corpus of data, a set of hypotheses, or candidate answers to the input question, are generated by looking across the corpus of data for portions of the corpus of data that have some potential for containing a valuable response to the input question.

The IBM Watson™ QA system then performs deep analysis on the language of the input question and the language used in each of the portions of the corpus of data found during the application of the queries using a variety of reasoning algorithms. There may be hundreds or even thousands of reasoning algorithms applied, each of which performs different analysis, e.g., comparisons, and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question based on the specific area of focus of that reasoning algorithm. Each resulting score is then weighted against a statistical model. The statistical model captures how well the reasoning algorithm performed at establishing the inference between two similar passages for a particular domain during the training period of the IBM Watson™ QA system. The statistical model may then be used to summarize a level of confidence that the IBM Watson™ QA system has regarding the evidence that the potential response, i.e. candidate answer, is inferred by the question. This process may be repeated for each of the candidate answers until the IBM Watson™ QA system identifies candidate answers that surface as being significantly stronger than others and thus, generates a final answer, or ranked set of answers, for the input question. More information about the IBM Watson™ QA system may be obtained, for example, from the IBM Corporation website, IBM Redbooks, and the like. For example, information about the IBM Watson™ QA system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

Types of information handling systems that can utilize QA system 100 range from small handheld devices, such as handheld computer/mobile telephone 110 to large mainframe systems, such as mainframe computer 170. Examples of handheld computer 110 include personal digital assistants (PDAs), personal entertainment devices, such as MP3 players, portable televisions, and compact disc players. Other examples of information handling systems include pen, or tablet, computer 120, laptop, or notebook, computer 130, personal computer system 150, and server 160. As shown, the various information handling systems can be networked together using computer network 102. Types of computer network 102 that can be used to interconnect the various information handling systems include Local Area Networks (LANs), Wireless Local Area Networks (WLANs), the Internet, the Public Switched Telephone Network (PSTN), other wireless networks, and any other network topology that can be used to interconnect the information handling systems. Many of the information handling systems include nonvolatile data stores, such as hard drives and/or nonvolatile memory. Some of the information handling systems shown in FIG. 1 depicts separate nonvolatile data stores (server 160 utilizes nonvolatile data store 165, and mainframe computer 170 utilizes nonvolatile data store 175. The nonvolatile data store can be a component that is external to the various information handling systems or can be internal to one of the information handling systems. An illustrative example of an information handling system showing an exemplary processor and various components commonly accessed by the processor is shown in FIG. 2.

Figure 2:
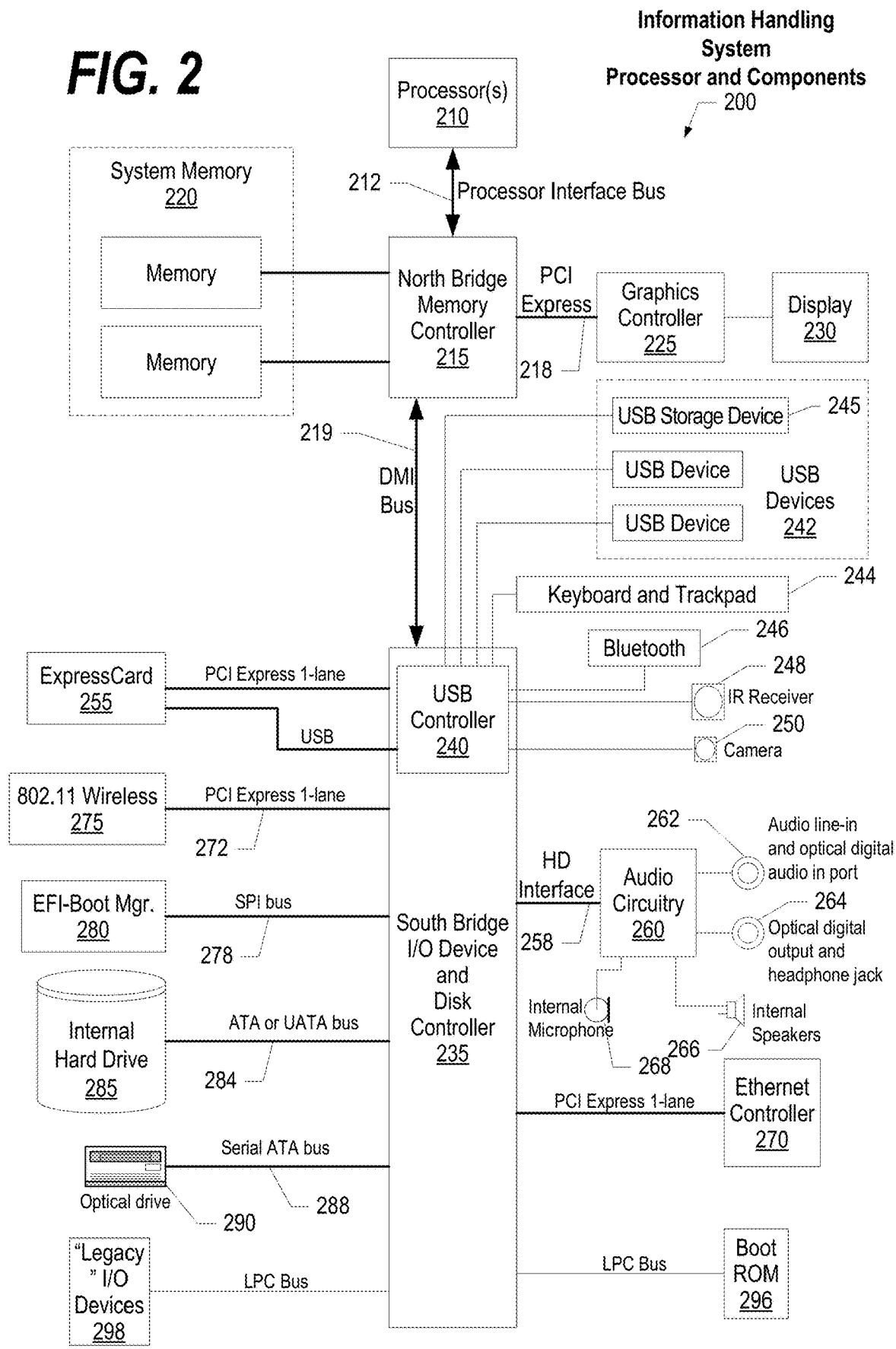
FIG. 2 illustrates an information handling system, more particularly, a processor and common components, which is a simplified example of a computer system capable of performing the computing operations described herein.

FIG. 2 illustrates information handling system 200, more particularly, a processor and common components, which is a simplified example of a computer system capable of performing the computing operations described herein. Information handling system 200 includes one or more processors 210 coupled to processor interface bus 212. Processor interface bus 212 connects processors 210 to Northbridge 215, which is also known as the Memory Controller Hub (MCH). Northbridge 215 connects to system memory 220 and provides a means for processor(s) 210 to access the system memory. Graphics controller 225 also connects to Northbridge 215. In one embodiment, PCI Express bus 218 connects Northbridge 215 to graphics controller 225. Graphics controller 225 connects to display device 230, such as a computer monitor.

Northbridge 215 and Southbridge 235 connect to each other using bus 219. In one embodiment, the bus is a Direct Media Interface (DMI) bus that transfers data at high speeds in each direction between Northbridge 215 and Southbridge 235. In another embodiment, a Peripheral Component Interconnect (PCI) bus connects the Northbridge and the Southbridge. Southbridge 235, also known as the I/O Controller Hub (ICH) is a chip that generally implements capabilities that operate at slower speeds than the capabilities provided by the Northbridge. Southbridge 235 typically provides various busses used to connect various components. These busses include, for example, PCI and PCI Express busses, an ISA bus, a System Management Bus (SMBus or SMB), and/or a Low Pin Count (LPC) bus. The LPC bus often connects low-bandwidth devices, such as boot ROM 296 and "legacy" I/O devices (using a "super I/O" chip). The "legacy" I/O devices (298) can include, for example, serial and parallel ports, keyboard, mouse, and/or a floppy disk controller. The LPC bus also connects Southbridge 235 to Trusted Platform Module (TPM) 295. Other components often included in Southbridge 235 include a Direct Memory Access (DMA) controller, a Programmable Interrupt Controller (PIC), and a storage device controller, which connects Southbridge 235 to nonvolatile storage device 285, such as a hard disk drive, using bus 284.

ExpressCard 255 is a slot that connects hot-pluggable devices to the information handling system. ExpressCard 255 supports both PCI Express and USB connectivity as it connects to Southbridge 235 using both the Universal Serial Bus (USB) the PCI Express bus. Southbridge 235 includes USB Controller 240 that provides USB connectivity to devices that connect to the USB. These devices include webcam (camera) 250, infrared (IR) receiver 248, keyboard and trackpad 244, and Bluetooth device 246, which provides for wireless personal area networks (PANs). USB Controller 240 also provides USB connectivity to other miscellaneous USB connected devices 242, such as a mouse, removable nonvolatile storage device 245, modems, network cards, ISDN connectors, fax, printers, USB hubs, and many other types of USB connected devices. While removable nonvolatile storage device 245 is shown as a USB-connected device, removable nonvolatile storage device 245 could be connected using a different interface, such as a Firewire interface, etcetera.

Wireless Local Area Network (LAN) device 275 connects to Southbridge 235 via the PCI or PCI Express bus 272. LAN device 275 typically implements one of the IEEE .802.11 standards of over-the-air modulation techniques that all use the same protocol to wireless communicate between information handling system 200 and another computer system or device. Optical storage device 290 connects to Southbridge 235 using Serial ATA (SATA) bus 288. Serial ATA adapters and devices communicate over a high-speed serial link. The Serial ATA bus also connects Southbridge 235 to other forms of storage devices, such as hard disk drives. Audio circuitry 260, such as a sound card, connects to Southbridge 235 via bus 258. Audio circuitry 260 also provides functionality such as audio line-in and optical digital audio in port 262, optical digital output and headphone jack 264, internal speakers 266, and internal microphone 268. Ethernet controller 270 connects to Southbridge 235 using a bus, such as the PCI or PCI Express bus. Ethernet controller 270 connects information handling system 200 to a computer network, such as a Local Area Network (LAN), the Internet, and other public and private computer networks.

While FIG. 2 shows one information handling system, an information handling system may take many forms, some of which are shown in FIG. 1. For example, an information handling system may take the form of a desktop, server, portable, laptop, notebook, or other form factor computer or data processing system. In addition, an information handling system may take other form factors such as a personal digital assistant (PDA), a gaming device, ATM machine, a portable telephone device, a communication device or other devices that include a processor and memory.

Figure 3:
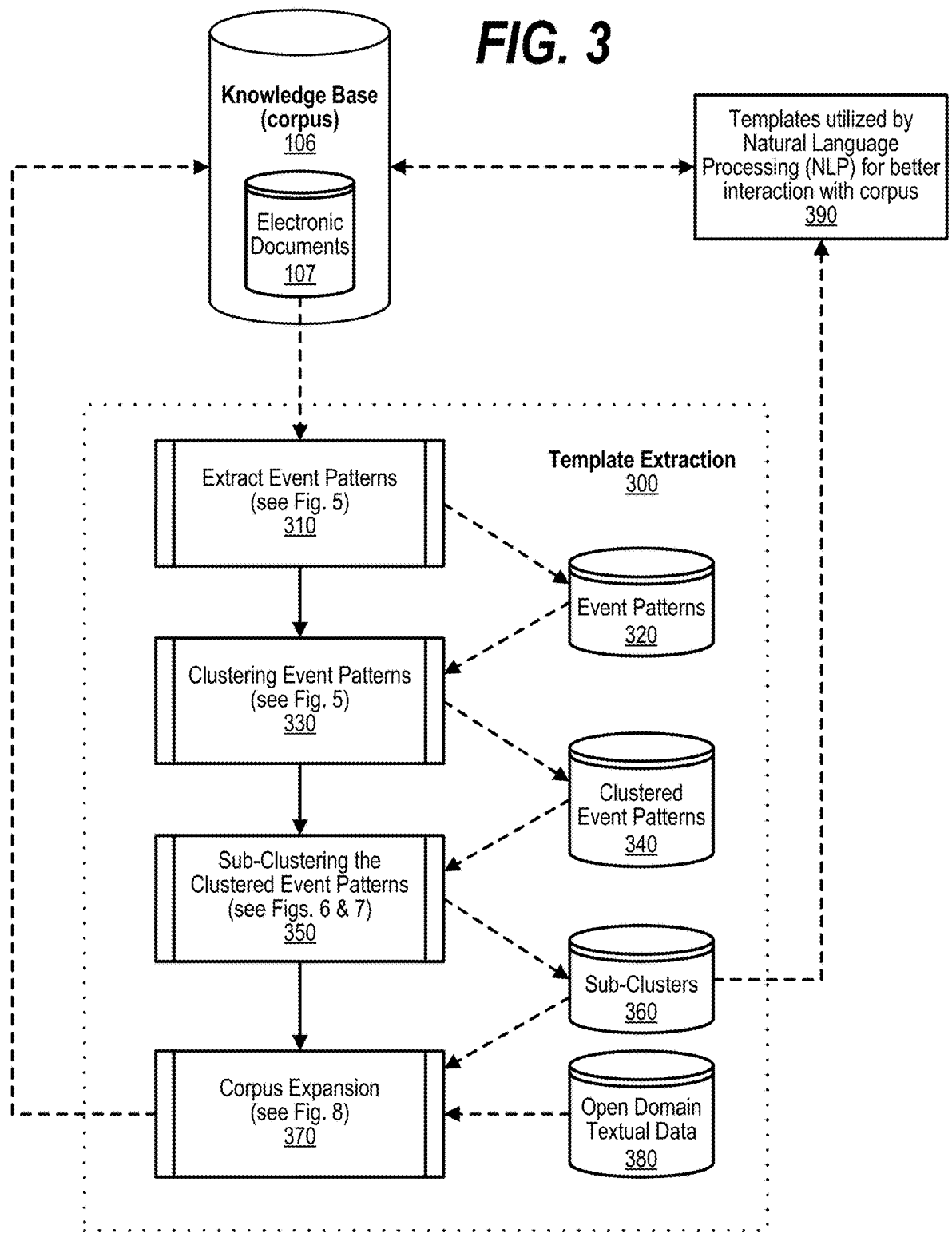
FIG. 3 is a high level flowchart showing higher-level steps performed to automatically extract templates.

FIG. 3 is a high level flowchart showing higher-level steps performed to automatically extract templates. Template extraction process 300 performs the high level steps shown to extract event patterns from corpus 106 utilized by a question answering (QA) system, analyzes the extracted event patterns to create a number of clusters of related event patterns, and creates relationship templates from the clusters of related event patterns. The created relationship templates are used to visually interact with the corpus. At predefined process 310, the process performs the Extract Event Patterns routine (see FIG. 5 and corresponding text for processing details). At predefined process 330, the process performs the Clustering Event Patterns routine (see FIG. 5 and corresponding text for processing details). At predefined process 350, the process performs the Sub-Clustering the Clustered Event Patterns routine (see FIGS. 6 and 7 and corresponding text for processing details). At predefined process 370, the process performs the Corpus Expansion routine (see FIG. 8 and corresponding text for processing details). At step 390, the process templates are utilized by Natural Language Processing (NLP) for better interaction with corpus 106.

Figure 4:
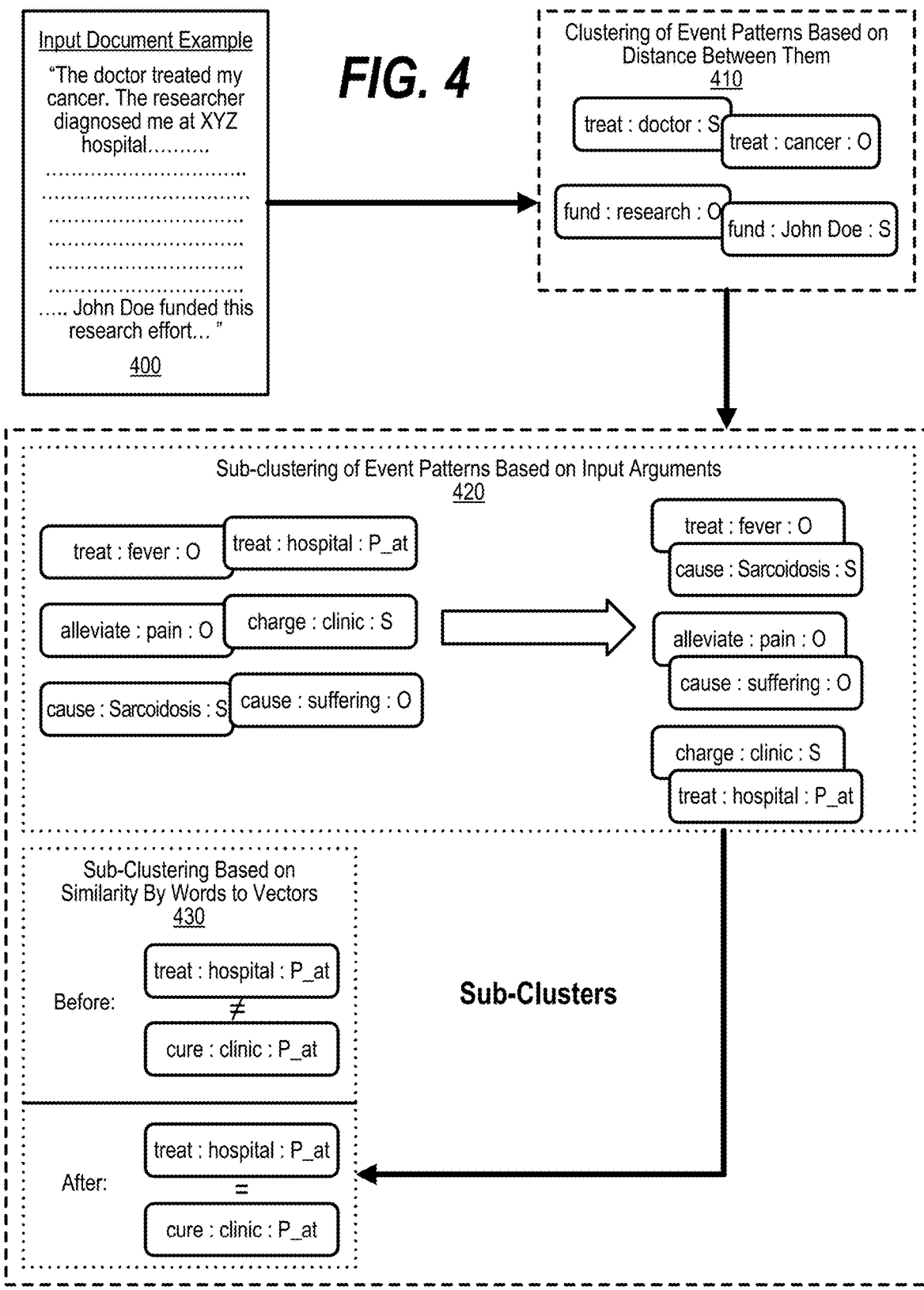
FIG. 4 is an diagram depicting clustering activities used to extract templates.

FIG. 4 is a diagram depicting clustering activities used to extract templates. FIG. 4 depicts an example that takes input text from input document 400, performs a Clustering of Event Patterns Based on Distance Between Them routine that results in example clusters that are shown in box 410. A Sub-clustering of Event Patterns Based on Input Arguments routine is then performed that results in the example sub-clusters shown in box 420. Finally, the Sub-Clustering Based on Similarity By Words to Vectors routine is performed to sub-cluster the data as shown in box 430.

Input document 400 shows an example from a patient that was treated for cancer at a particular hospital, with the research effort being funded by a person named "John Doe." The clustering of event patterns shown in box 410 shows different subject (S) and object (O) combinations. A first subject is that a doctor performed the treatment (treat: doctor) which is clustered with an object of what was treated, in this case cancer (treat: cancer). A second object being the research is clustered with the subject which is the person that funded the research ((fund: research) and (fund: John Doe)).

During sub-clustering, the event patterns are shown being sub-clustered based on input arguments in box 420. Here, example text is provided from input document, or documents, not shown in the text of document 400. In this example, event patterns ((treat: fever) clustered with (treat: hospital), (alleviate: pain) clustered with (charge: clinic), and (cause: Sarcoidosis) clustered with (cause: suffering)) are sub-clustered forming different sub-clusters. In this example, (treat: fever) is sub-clustered with (cause: Sarcoidosis), (alleviate: pain) is sub-clustered with (cause: suffering), and (charge: clinic) is sub-clustered with (treat: hospital). The events are sub-clustered based on input arguments provided to the algorithm.

Finally, box 430 depicts examples of sub-clustering that is based on similarity of words to vectors. In one embodiment, the arguments are converted into vectors using distributional semantics in order to judge the similarity between words. Traditional processes, such as the Word2vec process, can be used to generate the vectors corresponding to the words. A before and after example are provided to show the effect of applying sub-clustering that is based on similarity of words to vectors. Before, the event (treat: hospital) would not be clustered with event (cure: clinic). However, after applying sub-clustering that is based on similarity of words to vectors, these two events are found to have similar scores and are consequently clustered.

Figure 5:
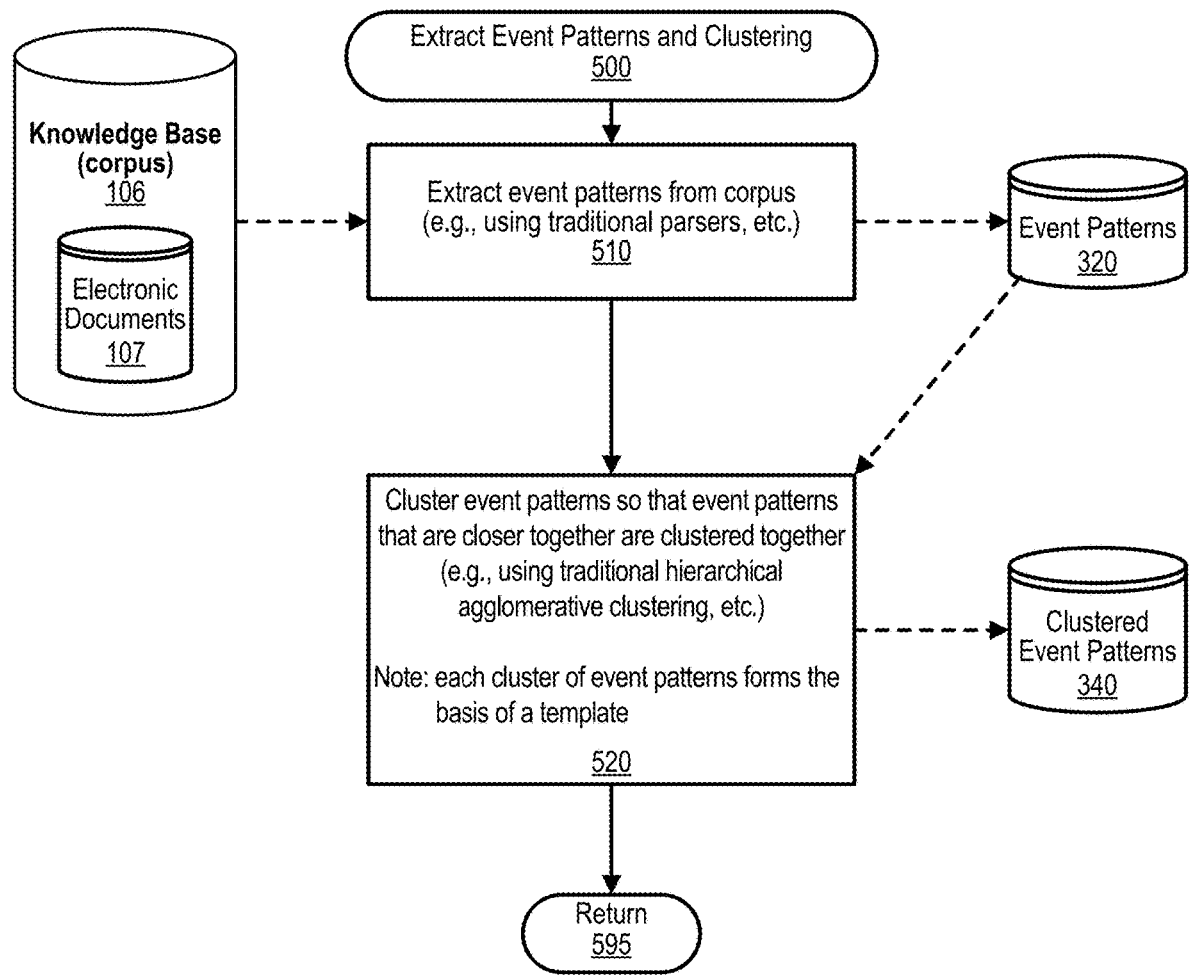
FIG. 5 is an exemplary flowchart that extracts event patterns and clusters the event patterns.

FIG. 5 is an exemplary flowchart that extracts event patterns and clusters the event patterns. FIG. 5 processing commences at 500 and shows the steps taken by a process that extracts event patterns and clusters the event patterns. At step 510, the process extracts event patterns from corpus 106, such as by using traditional parsers, etc. The extracted event patterns are stored in data store 320. At step 520, the process clusters event patterns so that event patterns that are closer together are clustered together. In one embodiment, the process uses traditional hierarchical agglomerative clustering techniques to cluster the event patterns. Note that each cluster of event patterns forms the basis of a relationship template. The clustered event patterns are then stored in data store 340. FIG. 5 processing thereafter returns to the calling routine (see FIG. 3) at 595.

Figure 6:
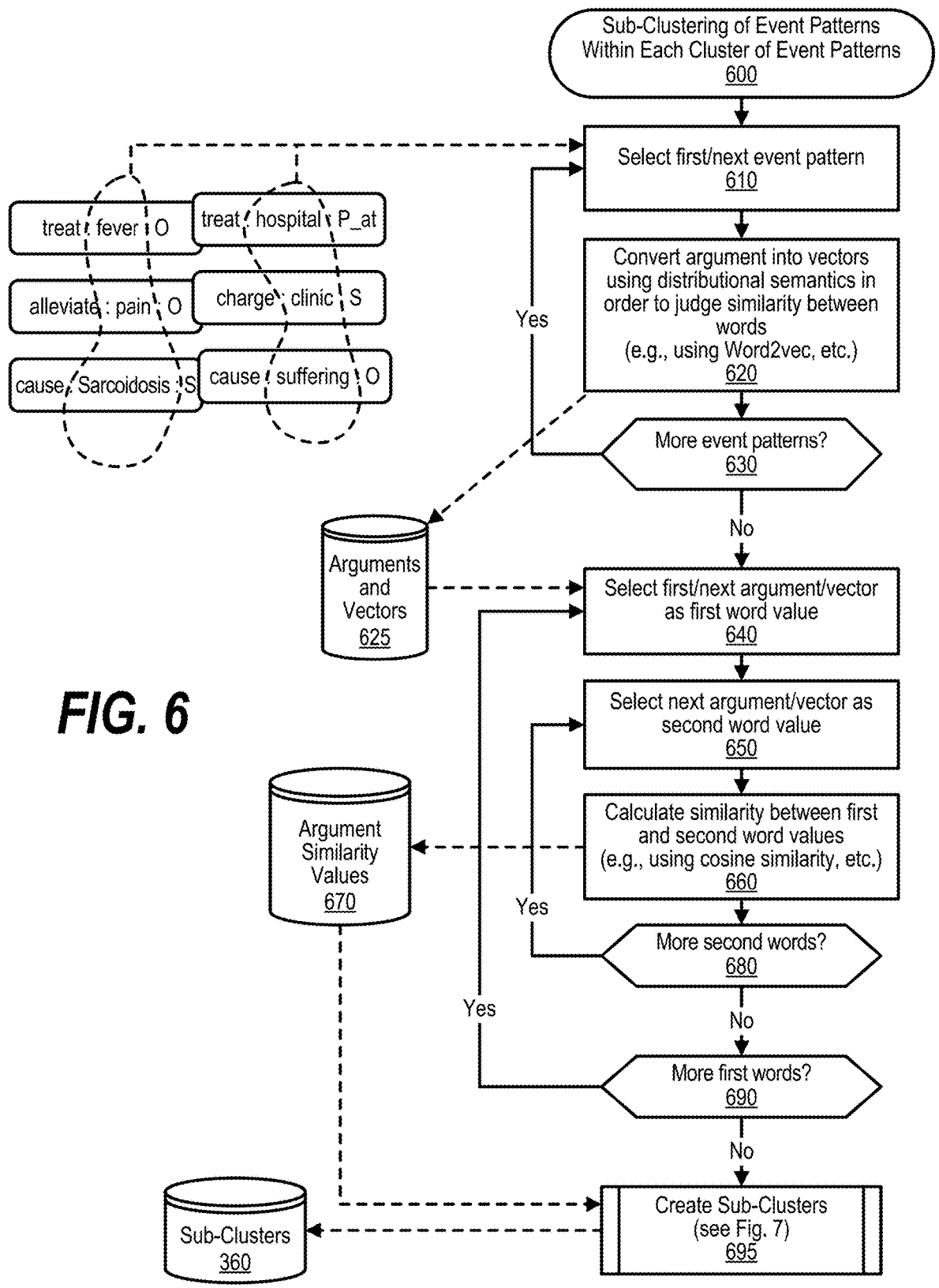
FIG. 6 is an exemplary flowchart that sub-clusters event patterns within each cluster of event patterns.

FIG. 6 is an exemplary flowchart that sub-clusters event patterns within each cluster of event patterns. FIG. 6 processing commences at 600 and shows the steps taken by a process that performs sub-clustering of event patterns within each cluster of event patterns. At step 610, the process selects the first event pattern that was extracted from the corpus. At step 620, the process converts argument into vectors using distributional semantics in order to judge the similarity between words. In one embodiment, the process uses the Word2vec process to convert the words into vectors. The arguments and their respective vectors are stored in data store 625.

The process determines as to whether there are more event patterns that need to be processed (decision 630). If there are more event patterns that need to be processed, then decision 630 branches to the 'yes' branch which loops back to step 610 to select and convert the next event pattern into vectors. This looping continues until there are no more event patterns to process, at which point decision 630 branches to the 'no' branch exiting the loop.

At step 640, the process selects the first argument/vector from data store 625 and treats the selected vector (word score) as the first word value. At step 650, the process selects next argument/vector from data store 625 and treats the selected vector (word score) as the second word value. At step 660, the process calculates the similarity between the first and second word values and stores the similarity value in data store 670. In one embodiment, the similarity values are determined using a cosine similarity algorithm.

The process determines as to whether there are more second words to compare to the first word (decision 680). If there are more second words, then decision 680 branches to the 'yes' branch which loops back to step 650 to select the next second word and compare it to the selected first word. This looping continues until there are no more second words, at which point decision 680 branches to the 'no' branch exiting the loop. The process determines as to whether there are more first words in data store 625 (decision 690). If there are more first words, then decision 690 branches to the 'yes' branch which loops back to step 640 to select the next first word from data store 625. This looping continues until there are no more first words to process, at which point decision 690 branches to the 'no' branch exiting the loop. At predefined process 695, the process performs the Create Sub-Clusters routine that creates sub-clusters and stores the sub-clusters in data store 360 (see FIG. 7 and corresponding text for processing details).

Figure 7:
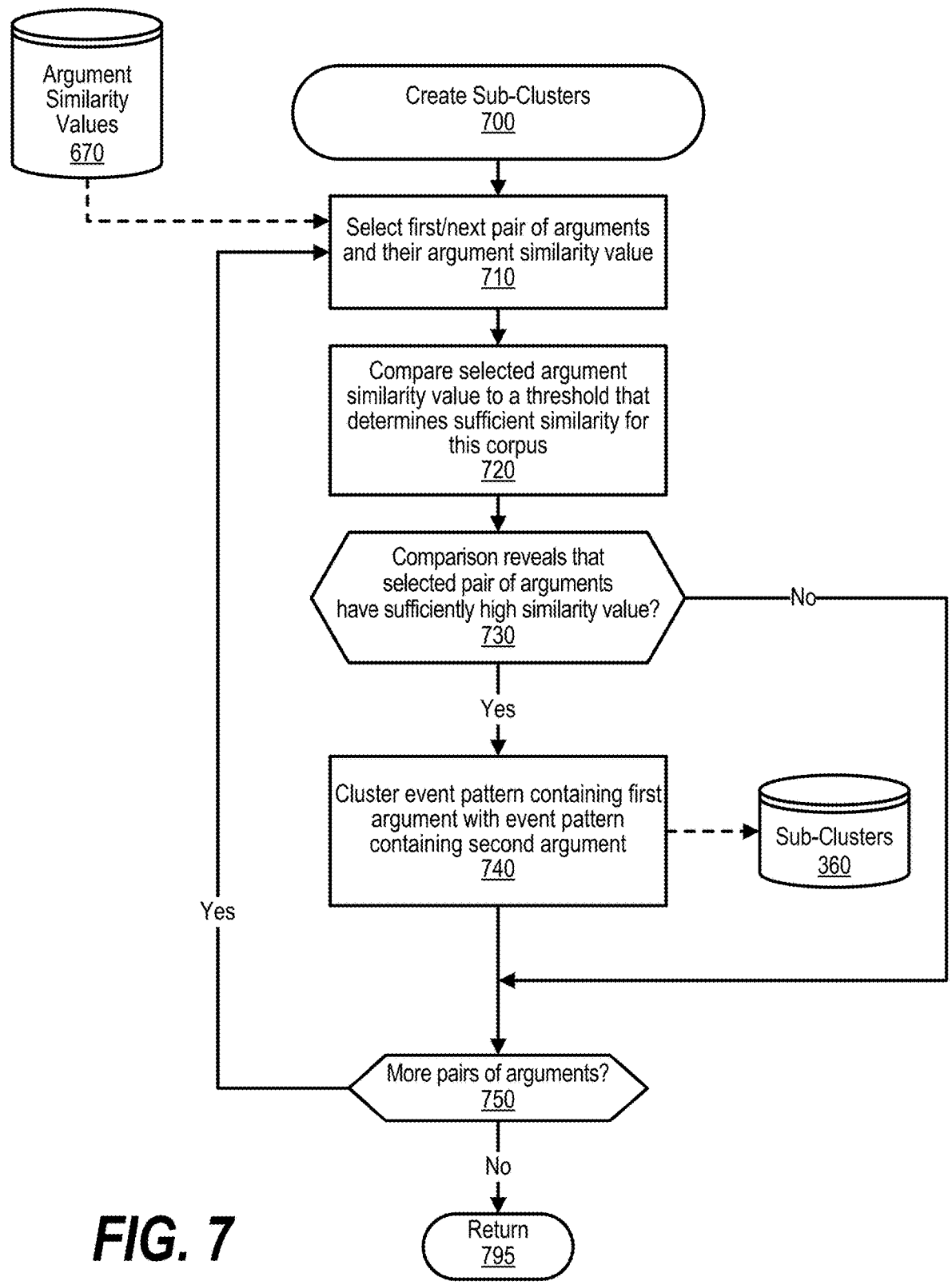
FIG. 7 is an exemplary flowchart that creates the sub-clusters.

FIG. 7 is an exemplary flowchart that creates the sub-clusters. FIG. 7 processing commences at 700 and shows the steps taken by a process that creates sub-clusters. At step 710, the process selects the first pair of arguments and their argument similarity value from data store 670. At step 720, the process compares the selected argument similarity value to a threshold that determines whether the arguments are sufficient similar for the corpus that is being utilized by this question answering (QA) system. The process determines as to whether the comparison reveals that the selected pair of arguments have a sufficiently high similarity value (decision 730). If the comparison reveals that the selected pair of arguments have a sufficiently high similarity value, then decision 730 branches to the 'yes' branch to perform step 740. On the other hand, if the comparison reveals that the selected pair of arguments does not have a sufficiently high similarity value, then decision 730 branches to the 'no' branch bypassing step 740. At step 740, the process clusters the event pattern that contains the first argument with the event pattern that contains the second argument.

The process determines as to whether there are more pairs of arguments to process (decision 750). If there are more pairs of arguments to process, then decision 750 branches to the 'yes' branch which loops back to step 710 to select and process the next pair of arguments as described above. This looping continues until there are no more pairs of arguments to process, at which point decision 750 branches to the 'no' branch exiting the loop. FIG. 7 processing thereafter returns to the calling routine (see FIG. 3) at 795.

Figure 8:
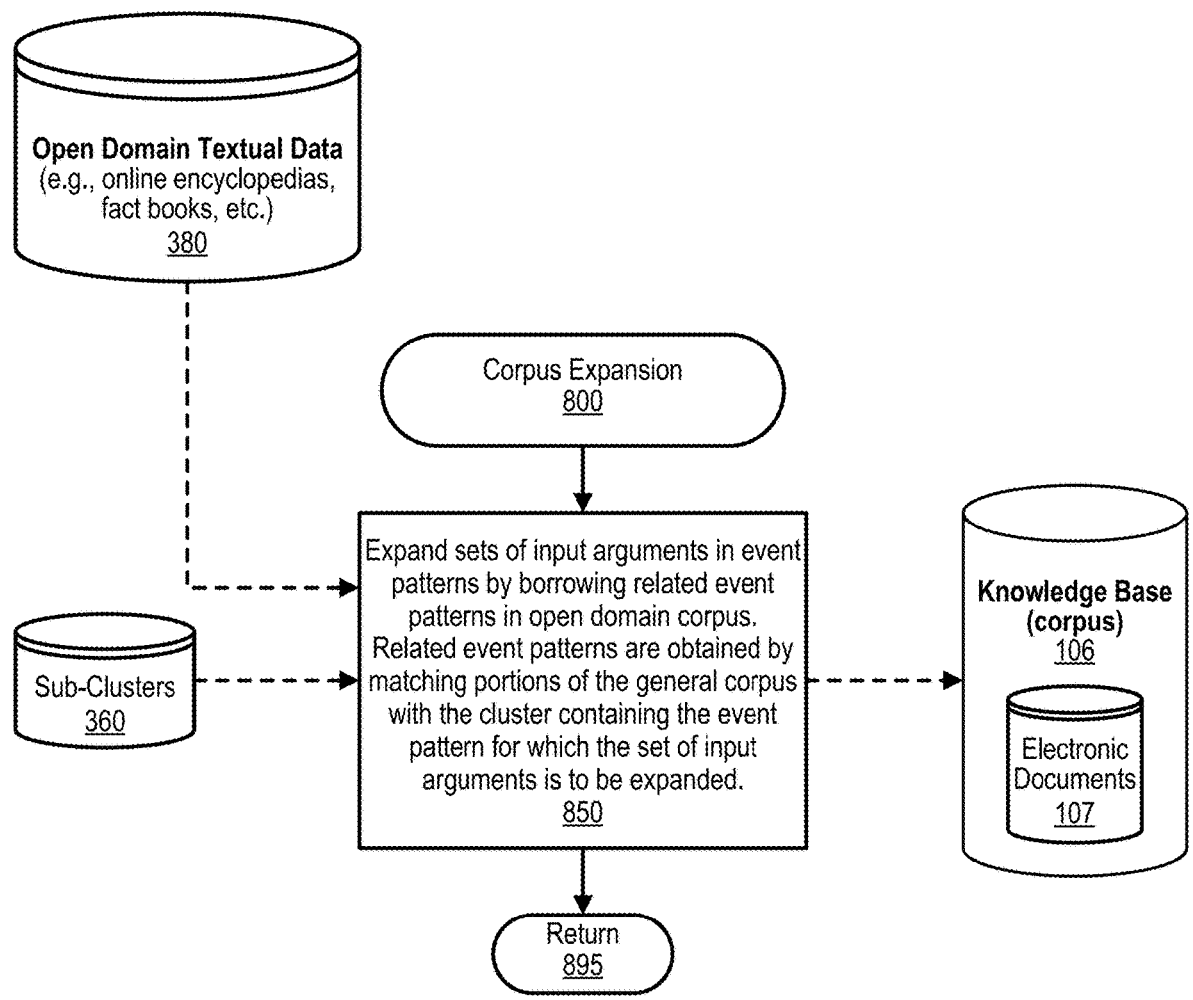
FIG. 8 is an exemplary flowchart that expands the corpus utilized by the question answering (QA) system.

FIG. 8 is an exemplary flowchart that expands the corpus utilized by the question answering (QA) system. FIG. 8 processing commences at 800 and shows the steps taken by a process that performs corpus expansion. At step 850, the process expands the sets of input arguments in the event patterns by borrowing related event patterns found in open domain corpus 380. The related event patterns are obtained by matching portions of the general corpus with the cluster containing the event pattern for which the set of input arguments is to be expanded. The sub-clusters that have been established are retrieved from data store 360. The expanded set of input arguments in the event patterns are stored in corpus 106. FIG. 8 processing thereafter returns to the calling routine (see FIG. 3) at 895.

Figure 9:
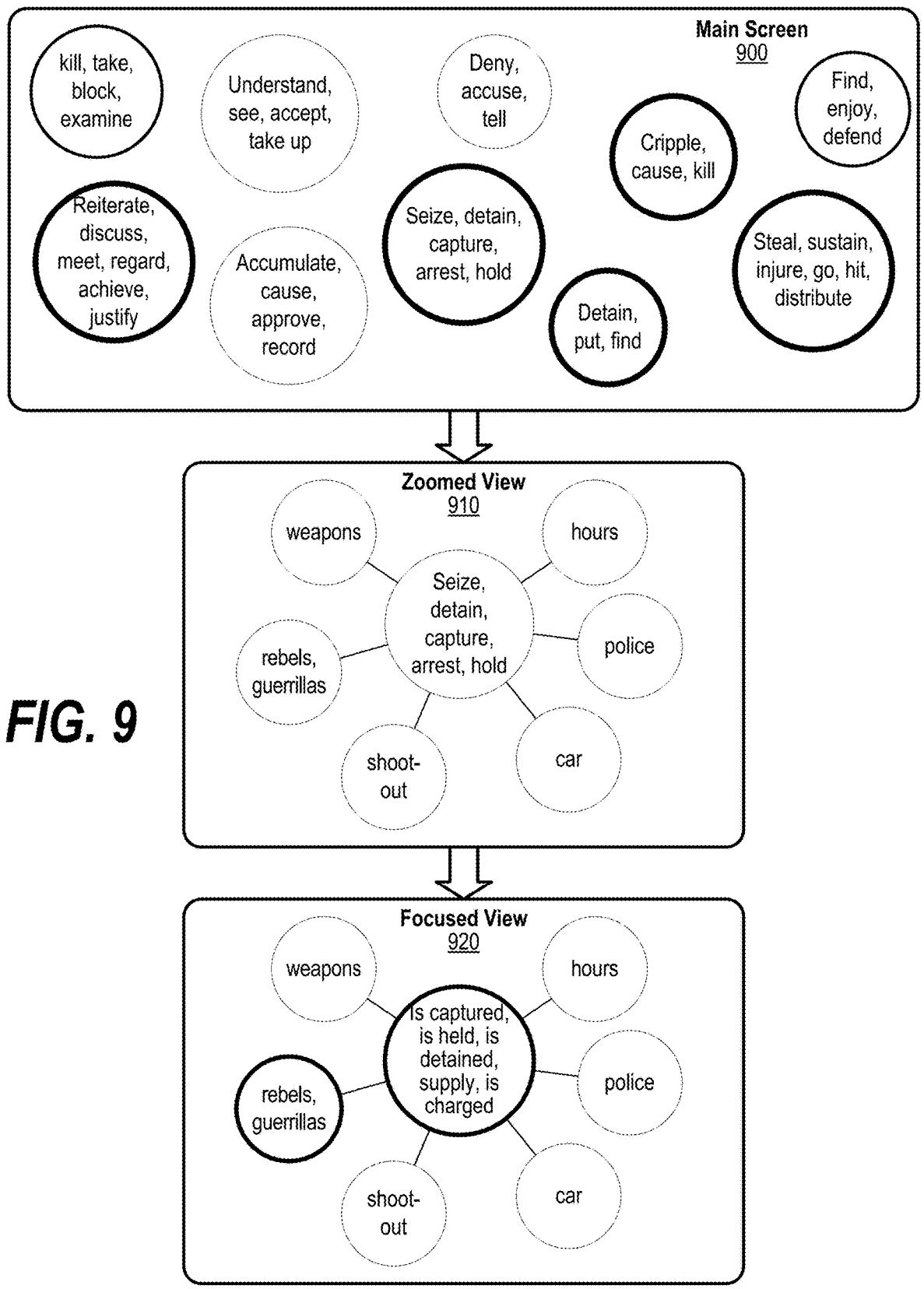
FIG. 9 shows an example user interface (UI) with three screens depicting a main view, a zoomed view, and a focused view.

FIG. 9 shows an example user interface (UI) with three screens depicting a main view, a zoomed view, and a focused view. Main screen 900 includes the templates extracted from the input text. Each template is represented by a circle in the main screen. The intensity, or weight, of the line forming the circle is directly proportional to the quality of the template. The heavier the line, the better the template. Each circle in the main screen includes the key events which occur in the template represented by the circle.

Zoomed view 910 shows a more detailed view of a template. It can be reached by selecting (e.g., "clicking," etc.) the circle representing the template from the main view. The zoomed view includes a large circle in the middle that includes the events in the template. The large circle in the middle is surrounded by multiple smaller circular islands, each of which represents a role within the template. Each circular island contains one or more examples of the role within the input corpus.

Focused view 920 is a more detailed view of a role within a template. This view can be reached by selecting (e.g., "clicking," etc.) one of the circular islands in the zoomed view. In this view, the clicked circular island might contain additional examples of the role that can be found in the input text. Instead of all the events in the template, the large central circle includes those events of which the selected role is a member.

In one embodiment, the tense of the verbs changes to show the relation of the role to the verb. If the role is a subject, the verb is in present tense. If the role is an object, then the verb is in passive voice. Finally, if the role is a prepositional object, the verb is in passive voice and the preposition involved is appended to the verb.

While particular embodiments of the present disclosure have been shown and described, it will be obvious to those skilled in the art that, based upon the teachings herein, that changes and modifications may be made without departing from this disclosure and its broader aspects. Therefore, the appended claims are to encompass within their scope all such changes and modifications as are within the true spirit and scope of this disclosure. Furthermore, it is to be understood that the disclosure is solely defined by the appended claims. It will be understood by those with skill in the art that if a specific number of an introduced claim element is intended, such intent will be explicitly recited in the claim, and in the absence of such recitation no such limitation is present. For non-limiting example, as an aid to understanding, the following appended claims contain usage of the introductory phrases "at least one" and "one or more" to introduce claim elements. However, the use of such phrases should not be construed to imply that the introduction of a claim element by the indefinite articles "a" or "an" limits any particular claim containing such introduced claim element to disclosures containing only one such element, even when the same claim includes the introductory phrases "one or more" or "at least one" and indefinite articles such as "a" or "an"; the same holds true for the use in the claims of definite articles.

The invention claimed is:

1. A method implemented by an information handling system that includes a memory and a processor, that improves a question answering (QA) computer system by automatically generating relationship templates, the method comprising:

extracting a plurality of event patterns corresponding to a plurality of events from data in a corpus utilized by the QA computer system;

analyzing the extracted event patterns resulting in a plurality of clusters of related event patterns;

creating one or more relationship templates from the plurality of clusters of related event patterns, wherein a first one of the or more relationship templates comprises a first set of the plurality of events included in a first one of the plurality of clusters;

displaying the first relationship template as a first graphical representation on a display, wherein the first graphical representation displays the first set of events; and in response to receiving an input selection that selects the first graphical representation, displaying a set of second graphical representations on the display that represent a set of roles within the first relationship template.

2. The method of claim 1 further comprising:

expanding the corpus utilized by the QA system, wherein the expanding further comprises:

receiving a plurality of text data outside the corpus;

retrieving a plurality of sub-clusters, wherein each of the sub-clusters is based on the created one or more relationship templates; and expanding a plurality of input arguments included in the event patterns by using a set of related event patterns found in the plurality of text data outside the corpus, wherein the method further comprises:

matching portions of the corpus with the cluster that includes the related event pattern corresponding to the plurality of input arguments.

3. The method of claim 1 wherein the extracting further comprises:

clustering the event patterns using hierarchical agglomerative clustering techniques so that the event patterns that are closer together are clustered in the same event pattern, wherein each cluster of event patterns forms the basis of one of the one or more relationship templates.

4. The method of claim 1 wherein the analyzing further comprises:

converting an argument in each of the extracted event patterns into vectors by using distributional semantics, wherein the converting results in a plurality of word values each corresponding to one of a plurality of words in the extracted event pattern;

calculating a similarity score between the plurality of words based on the word values pertaining to the respective words; and identifying a plurality of sets of similar words based on a comparison of the calculated similarities.

5. The method of claim 4 further comprising:

selecting each of the arguments and a successive argument to the selected argument; and calculating the similarity score between the selected argument and the successive argument.

6. The method of claim 5 further comprising:

performing the selecting and calculating on each pair of arguments and storing the similarity scores of all of the pairs;

comparing the similarity scores to a threshold;

in response to the threshold revealing a high similarity score between the arguments in one or more of the pairs of arguments:

clustering the event pattern corresponding with the selected arguments with the event pattern corresponding with the selected arguments' respective successive arguments.

7. The method of claim 5 wherein the similarity is calculated using a cosine similarity algorithm.

\* \* \* \* \*